United States Patent [19]

Hartle

[11] 3,953,498

[45] Apr. 27, 1976

[54] DIESTERS AND DIACIDS OF PHENANTHRENE

[75] Inventor: Robert J. Hartle, Gibsonia, Pa.

[73] Assignee: Gulf Research & Development Company, Pittsburgh, Pa.

[22] Filed: Nov. 13, 1974

[21] Appl. No.: 523,355

Related U.S. Application Data

[63] Continuation-in-part of Ser. No. 89,124, Nov. 12, 1970, abandoned, which is a continuation-in-part of Ser. No. 635,997, May 4, 1967, abandoned.

[52] U.S. Cl. ................. 260/475 FR; 204/158 HE; 260/346.3; 260/475 R; 260/515 P; 260/523 R
[51] Int. Cl.² .................. C07C 63/46; C07C 69/76
[58] Field of Search ................. 260/515 P, 475 FR

[56] References Cited

OTHER PUBLICATIONS

Elsevier's Encyclopedia of Organic Chemistry, Vol. 13, p. 989, (1946).

Danheux et al., as cited in Chem. Abstracts, 59, p. 3848, (1964).

Mallory et al., J. A. C. S. 86, pp. 3094–3095, (1964).

*Primary Examiner*—Anton H. Sutto
*Assistant Examiner*—Jane S. Myers

[57] ABSTRACT

Novel 1,8-, 2,7-, 3,6- and 2,5-diesters and diacids of phenanthrene.

9 Claims, No Drawings

DIESTERS AND DIACIDS OF PHENANTHRENE

This application is a continuation-in-part of my copending Patent Application Ser. No. 89,124, filed Nov. 12, 1970, now abandoned, which was in turn a continuation-in-part of Patent Application Ser. No. 635,997, filed May 4, 1967, now abandoned.

This invention relates to novel phenanthrene diester and diacid compounds, namely, the 1,8-, 2,7-, 3,6- and 2,5-phenanthrene diesters and the 1,8-, 2,7-, 3,6- and 2,5-phenanthrene dicarboxylic acids.

The two ring structures in the stilbene molecule join together in a substitution reaction at the ortho-position to form phenanthrene, a fused ring structure, by irradiation with ultraviolet light in the presence of suitable oxidants. This photocyclization is carried out by irradiating stilbene in a suitable stilbene solvent which transmits ultraviolet light of the desired wavelength and which is stable to the ultraviolet light such as cyclohexane. It has been shown that nuclear substituted stilbenes, particularly containing those ring substituents which are known activators for further ring substitution such as methyl, methoxy and phenyl and also α-carboxyl substituted stilbene can be cyclized in the ortho-substitution reaction to the corresonding fused ring phenanthrene compound. However, it has been further determined that stilbenes containing nuclear substituents which strongly deactivate the benzene ring against further substitution such as nitro and acetyl groups have not been successfully photochemically converted to their phenanthrene counterpart.

The photocyclization of ring-substituted carboxy stilbenes has not been reported. This lack of success is not surprising for two reasons, first due to the insolubility of nuclear-substituted carboxy stilbenes in the reaction solvent (4,4'-stilbenedicarboxylic acid has a solubility in cyclohexane less than 0.001 g./100 ml. at 25°C.) and second, due to the well recognized strong deactivating effect of the nuclear carboxyl group against further ring substitution. Since nuclear ester groups are also well known to be strong deactivators of the benzene ring, it would be expected that nuclear ester groups would also effectively prevent photocyclization of the substituted stilbene similarly to the carboxyl, acetyl and nitro ring deactivators. However, I have surprisingly discovered that certain dinuclear, diester stilbenes can be effectively cyclized to the corresponding novel phenanthrene diester compounds.

I have discovered that diesters of the symmetrical, aromatic ring-substituted diacids of stilbene can be converted while in solution to the corresponding diesters of phenanthrene by ultraviolet light. For example, the 2,2' diesters of stilbene are converted to the 1,8diesters of phenanthrene, the 3,3' diesters of stilbene are converted to a mixture of the 2,5 and 2,7 diesters of phenanthrene and the 4,4' diesters of phenanthrene are converted to the 3,6 diesters of phenanthrene. These resulting diesters of phenanthrene can then be converted to the corresponding diacids of phenanthrene by a saponification process. I have further discovered that the 4,5 diesters of phenenthrene are not obtained by this procedure.

The stilbene diester compounds employed are symmetrical in structure and are mono-substituted in the ortho, meta or para position on each aromatic ring of the stilbene molecule. The stilbene esters that are employed herein can be defined structurally as follows:

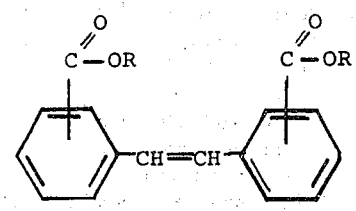

wherein R is selected from the group consisting of alkyl, alkoxyalkyl, cycloalkyl and aralkyl radicals having from one to 12 carbon atoms, preferably from one to four carbon atoms. Specific examples of such stilbene esters include dimethyl 4,4'-stilbenedicarboxylate, diethyl 4,4'-stilbenedicarboxylate, di-n-propyl 4,4'-stilbenedicarboxylate, di-isopropyl 4,4'-stilbenedicarboxylate, di-n-butyl 4,4'-stilbenedicarboxylate, di-isobutyl 4,4'-stilbenedicarboxylate, di-tert-butyl 4,4'-stilbenedicarboxylate, di-n-amyl 4,4'-stilbenedicarboxylate, di-iso-amyl 4,4'-stilbenedicarboxylate, di-n-hexyl 4,4'-stilbenedicarboxylate, di-2-ethylbutyl 4,4'-stilbenedicarboxylate, di-n-heptyl 4,4'-stilbenedicarboxylate, di-n-octyl 4,4'-stilbenedicarboxylate, di-iso-octyl 4,4'-stilbenedicarboxylate, di-n-decyl 4,4'-stilbenedicarboxylate, di-n-dodecyl 4,4'-stilbenedicarboxylate, di-cyclohexyl 4,4'-stilbenedicarboxylate, di-methoxyethyl 4,4'-stilbenedicarboxylate, di-ethoxyethyl 4,4'-stilbenedicarboxylate, di-butoxyethyl 4,4'-stilbenedicarboxylate and di-benzyl 4,4'-stilbenedicarboxylate. Additionally, these ester compounds can be substituted in the 2,2' and 3,3' positions on the stilbene radical. Thus I can use as starting materials diesters of 2,2', 3,3' or 4,4' stilbenedicarboxylic acid.

The aromatic ring-substituted dicarboxylate of stilbene to be converted, before being irradiated, is solubilized in a suitable organic solvent. Any solvent in which the diester will dissolve rather easily, is inert under the reaction conditions, and will permit the passage of radiant energy therethrough, as defined below, can be employed in the photocyclization reaction. Examples of such solvents are cyclohexane, benzene, methylene chloride, and the like.

Irradiation of these ring-substituted diesters of stilbenedicarboxylic acid can be effected by any source of ultraviolet radiation of suitable wavelength either naturally or artificially produced. I have found commercially available mercury vapor discharge lamps, which emit light having wavelengths from about 2,000 to about 4,000 A and have wattage ratings of from about 450 to 500 watts, to be especially useful in carrying out the reaction. Specific examples of such lamps are Hanovia high-pressure quartz mercury-vapor lamps 673 A. and 679 A.

The diester of stilbene is not irradiated alone but in combination or in admixture with a controlled amount of an oxidizing agent. By "oxidizing agent" I mean to inclue any reagent capable of removing two hydrogen atoms from the postulated dihydrophenanthrene intermediate to form a phenanthrene structure. A preferred oxidizing agent is oxygen which is maintained in the reaction mixture in excess by bubbling air through the reaction mixture. Additionally, a catalytic amount of an auxiliary oxidizing agent, such as iodine can be added to speed up the reaction. The amount of auxiliary oxidizing agent required can vary over wide limits, for example, from about one to about 25 mole percent, preferably from about five to about 10 mole percent based on the diester of stilbenedicarboxylic acid. The amount of time required for such irradiation can be from about one to about 20 hours, preferably from about six to about 12 hours.

The novel phenanthrene diesters prepared by irradiation of the stilbene precursors are produced in four different isomeric configurations, depending upon the particular stilbene compound used as the starting material. The stilbene precursors with the corresponding phenanthrene diesters are listed.

| Stilbene Precursor | Phenanthrene Diester |
|---|---|
| 2,2' stilbene diester | : 1,8 phenanthrene diester |
| 3,3' stilbene diester | : 2,7 phenanthrene diester |
|  | 2,5 phenanthrene diester |
| 4,4' stilbene diester | : 3,6 phenanthrene diester |

Although the 4,5 diester of phenanthrene is theoretically possible from the 3,3' diester of stilbene, I have found that it is not produced by the described process.

The novel product of the photochemical reaction is structurally identified as follows:

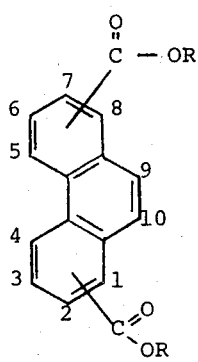

where R is selected from the group consisting of alkyl, alkoxyalkyl, cycloalkyl and aralkyl radicals as defined above and the ester substituents in the phenanthrene molecule are located in the numbered positions set out in the above list.

The novel phenanthrene diesters thus produced are recovered by any suitable means, such as by evaporation of the solvent and recrystallization from benzene or cyclohexane. As will be noted from the above list, treatment of 3,3' diesters of stilbene results in the production of a mixture of 2,7 and 2,5 diester isomers of phenanthrene. These isomers can be separated by conventional methods, such as, for example, fractional crystallization, molecular distillation, gas phase chromatography, and chromatographic adsorption on alumina or silica.

These diesters of phenanthrene are thereafter converted to their corresponding diacids by conventional methods such as saponifying them with alkali followed by acidification to precipitate the diacid. This saponification can be effected by solubilizing the diester in a suitable solvent, such as ethanol, and thereafter adding five to 10 percent by weight of the diester of a 10 to 20 percent sodium or potassium hydroxide solution and refluxing the mixture from about four to six hours at 100° C. The novel phenanthrene dicarboxylic acid has the carboxyl substituents in the same position as the ester substituents in the parent phenanthrene diester compound.

Thereafter, the phenanthrene diacids obtained can be converted to diphenyltetracarboxylic acids by oxidation with suitable oxidizing agents such as a mixture of sodium dichromate and sulfuric acid. For example, oxidation can be effected by slowly adding one part of the phenanthrene dicarboxylic acid to a mixture of 15 parts of concentrated sulfuric acid, 25 parts water and 10 parts sodium dichromate and stirring the resulting mixture at 100° to 110° C. for about four hours. For example, 1,8 phenanthrenedicarboxylic acid is converted to 2,2', 3,3' diphenyltetracarboxylic acid. This latter compound can then be converted to the corresonding dianhydride.

The novel phenanthrene diesters can also be oxidized to produce diesters of diphenyltetracarboxylic acids and these compounds can then in turn be converted to dipheyltetracarboxylic acids by suitable methods such as saponification. These novel phenanthrene diesters can be oxidized with suitable oxidizing agents such as, for example, a mixture of acetic acid and chromic acid to obtain favorable yields of diesters of diphenyltetracarboxylic acids without appreciable degradation of the ester groups. In carrying out this oxidation reaction diesters of phenanthraquinone dicarboxylic acid are also obtained. The ratio of quinone product to acid product obtained upon oxidation is dependent upon the oxidizing conditions of the reaction. That is, milder oxidizing conditions utilizing lower concentrations of oxidizing agent and lower reaction temperatures produce a higher ratio of quinone compound while more severe oxidizing conditions result in higher diester-acid production. These diesters of diphenyltetracarboxylic acid can in turn be easily converted by conventional methods such as, for example, saponification to produce diphenyltetracarboxylic acids.

All of the isomers of diphenyltetracarboxylic acids produced as described above contain carboxyl groups in the 2,2' positions. Other carboxyl groups can occupy the 3,3'; 4,4'; 5,5'; or 4,6' positions depending on the position of the carboxyl groups in the starting compound. Cyclic anhydrides can be formed from any pair of adjacent carboxyl groups such as those in the 2,3 and 2,3' positions. Thus a dianhydride can be formed from the 2,2',3,3' isomer of diphenyltetracarboxylic acid while monoanhydrides can be obtained from the 2,2',4-,4'; 2,2',5,5' and 2,2',4,6' isomers. Anhydride formation can be accomplished by heating the particular diphenyltetracarboxylic acid with acetic anhydride, acetyl chloride or phosphorous oxychloride.

These diphenyltetracarboxylic acids and anhydrides can be used as cross-linking agents for epoxy resins and as starting materials for the production of other valuable resins such as polyimides. In addition, the diphenyltetracarboxylic acids and novel phenanthrene diesters of this invention can be used in the preparation of polyester compounds My invention will be further explained by the following illustrative examples:

EXAMPLES 1 to 9

Conversion of Diesters of Stilbene to Phenanthrenedicarboxylic Acids

Several alkyl diesters of stilbene were irradiated with ultraviolet light in the presence of an oxidizing agent to form the corresponding phenanthrene diester and thereafter these esters were isolated and converted to acids by saponification with alkali.

The apparatus employed in the photochemical conversion consisted of a cylindrical pyrex flask of approximately two-liter capacity, into the center neck of which was placed a "Vycor" glass well. The well was of double wall construction to permit circulation of cooling water and extended approximately nine inches into the flask. The ultraviolet source, a 550 watt, No. 673 Hanovia high-pressure mercury vapor lamp, was contained inside the well. The flask was also equipped with a magnetic stirrer, thermometer, reflux condenser, and gas inlet tube. The particular stilbene diester to be irradiated was mixed at a concentration of three to eight grams/liter of a solvent (cyclohexane or methylene chloride) and placed in the flask along with 0.1 to 0.2 gram of iodine and a slow stream of air was passed through the solution. The irradiation was carried out at ambient temperature or slightly above (25° to 35° C.), from about eight hours to about 27 hours.

The phenanthrene diesters produced by the irradiation were recovered by evaporation of the solvent at reduced pressure and recrystallization from benzene or cyclohexane. The diesters were then converted to the free acids by refluxing 10 grams of the ester in 250 grams of 10 percent potassium hydroxide solution for approximately four hours. The acids were precipitated out by acidifying the solution. Table I below summarizes the results of these runs.

EXAMPLE 10

Oxidation of Phenanthrenedicarboxylic Acids to Diphenyltetracarboxylic Acids

A mixture of 15.3 grams of concentrated sulfuric acid, 25 ml of water, and 10 grams of sodium dichromate was heated to 100° C. 1.0 gram of 3,6-phenanthrenedicarboxylic acid (obtained by the procedures outlined in Examples 1 to 9) was added to the oxidizing solution over a 15 minute period. The mixture was held at 100° to 110° C. for four hours with stirring, and then poured over ice. A solid precipitated out and was washed with water and slurried with 50 ml of five percent sodium bisulfite solution to remove possible quinone intermediate. The solid was then dissolved in ammonium hydroxide, filtered and the acid precipitated with hydrochloric acid. After washing and drying of the product, the solid had a melting point of 390° C. and was analyzed as 2,2′,5,5′-diphenyltetracarboxylic acid.

Analysis of this compound was as follows: Calculated for $C_{16}H_{10}O_8$: NE, 82.6; C, 58.19; H, 3.05. Found: NE, 81.1; C, 57.55; H, 3.13.

EXAMPLE 11

Oxidation of Diesters of Phenanthrene and Conversion of Resulting Product to Diphenyltetracarboxylic Acid Ten grams of 3,6-di-n-butyl phenanthrenedicarboxylate were dissolved in 400 milliliters of warm glacial Table I

| Starting Compound | Concentration g/liter | Solvent | Irradiation Time, hrs. | % Yield Phenanthrene Dicarboxylic Acid |
|---|---|---|---|---|
| Diethyl ester of 4,4′-stilbenedicarboxylic acid | 6.7[1] | 1500 ml cyclohexane | 26 | 60 |
| Diethyl ester of 4,4′-stilbenedicarboxylic acid | 6.7[1] | 1500 ml methylene chloride | 22 | 40 |
| Diethyl ester of 4,4′-stilbenedicarboxylic acid | 3.3 | 1500 ml cyclohexane | 22 | 90 crude (mp 155° C.) |
| Diethyl ester of 4,4′-stilbenedicarboxylic acid | 3.3 | 1500 ml cyclohexane | 18 | 50 recrystallized |
| Diethyl ester of 4,4′-stilbenedicarboxylic acid | 3.0 | 1500 ml cyclohexane | 8 | 54 recrystallized |
| Di-n-butyl ester of 4,4′-stilbenedicarboxylic acid | 7.7 | 1300 ml cyclohexane | 17[2] | 50 recrystallized |
| Di-n-butyl ester of 4,4′-stilbenedicarboxylic acid | 6.3 | 4000 ml cyclohexane | 9 | 50 recrystallized |
| Dimethyl ester of 2,2′-stilbenedicarboxylic acid | 1.8 | 1500 ml cyclohexane | 24 | 60 |
| Diethyl ester of 2,2′-stilbenedicarboxylic acid | 2.0 | 1500 ml cyclohexane | 8 | 60 |

[1]Stilbene diester not completely soluble at room temperature.
[2]Ultraviolet spectra of reaction mixture indicated that very little reaction occurs after the first six hours of irradiation.

The phenanthrene structure of the acids produced by the method previously described was identified by decarboxylation with copper carbonate-quinoline solution as follows. Approximately 0.5 gram of the free acid obtained from the irradiation product of the diethyl ester of 4,4′-stilbenedicarboxylic acid was added to 10 ml of quinoline containing 0.1 gram of cupric carbonate. The mixture was refluxed for two hours, cooled and diluted with 25 ml of ether. The mixture was filtered and the filtrate washed with dilute hydrochloric acid followed by a water wash. Evaporation of the ether left 0.45 gram of pale yellow plates having a melting point of 75° to 80° C. Recrystallization from ethanol increased the melting point to 94° to 95° C. The product was identified as phenanthrene by melting point and infrared spectral analysis.

acetic acid. To this solution was added, in small portions, 30 grams of chromic acid and the resulting mixture was heated to 100° C. and refluxed at this temperature for one hour. Thereafter, the mixture was cooled and poured into ice water. A solid product was obtained which was washed with water and extracted with 300 milliliters of 10 percent sodium bicarbonate solution. An insoluble product remained after extraction which was washed with water, dried, and recrystallized from ethanol-benzene to give di-n-butyl-(9,10-phenanthraquinone)-3,6-dicarboxylate as golden plates having a melting point of 148°C.

Analysis of this compound was as follows: Calculated for $C_{24}H_{24}O_6$: C, 70.57; H, 5.92. Found: C, 70.51; H, 5.85.

The extract was then acidified and the resulting precipitate was removed on a filter, washed with water, and dried under vacuum. Recrystallization of the solid from ethanol-hexane gave the 5,5'-dibutyl ester of 2,2',5,5'-diphenyltetracarboxylic acid as white prisms having a melting point of 223° C.

Analysis of this compound was as follows: Calculated for $C_{24}H_{26}O_8$ : C, 65.15; H, 5.92. Found: C, 64.63; H, 5.79.

The resulting 5,5'-diester of diphenyltetracarboxylic acid produced by the above oxidation was then converted to 2,2',5,5'-diphenyltetracarboxylic acid by the saponification procedures set forth in Examples 1 to 9.

EXAMPLES 12 TO 13

Formation of Anhydrides of Diphenyltetracarboxylic Acids

One mole of 2,2',5,5'-diphenyltetracarboxylic acid was mixed with three moles of acetic anhydride in 200 milliliters of acetic acid. The mixture was refluxed for approximately two hours, cooled, filtered and washed with approximately 500 milliliters of glacial acetic acid. The resulting monoanhydride was dried at 125° to 150° C. for four hours in a vacuum oven.

The dianhydride of 2,2',3,3'-diphenyltetracarboxylic acid was prepared by heating the acid at 180° to 190° C. for three to four hours under vacuum.

In like manner di-n-octyl 2,2'-stilbenedicarboxylate is converted to di-n-octyl 1,8-phenanthrenedicarboxylate and this is then converted to 1,8-phenanthrenedicarboxylic acid, di-n-dodecyl 2,2'-stilbenedicarboxylate is converted to di-n-dodecyl 1,8-phenanthrenedicarboxylate and this is then converted to 1,8-phenanthrenedicarboxylic acid, di-cyclohexyl 3,3'-stilbenedicarboxylate is converted to a mixture of di-cyclohexyl 2,7-phenanthrenedicarboxylate and di-cyclohexyl 2,5-phenanthrenedicarboxylate and these are then converted to a mixture of 2,7-phenanthrenedicarboxylic acid and 2,5-phenanthrenedicarboxylic acid, and di-benzyl 4,4'-stilbenedicarboxylate is converted to di-benzyl 3,6-phenanthrenedicarboxylate and then to 3,6-phenanthrenedicarboxylic acid. Also additional members of the above described stilbene diesters are converted to the corresponding phenanthrene diesters and diacids in a similar manner. Other suitable solvents and oxidizing agents can be used in producing these compounds.

Although specific examples of the invention have been set forth hereinabove, it is not intended to limit the invention thereto, but to include all of the variations and modifications falling within the scope of the appended claims.

I claim:

1. A phenanthrene diester selected from the group consisting of 1,8-, 2,7-, 3,6- and 2,5-phenanthrene diesters, said diester having the formula:

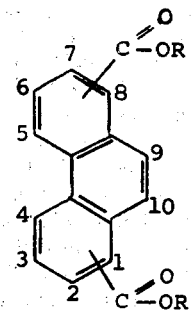

wherein R has from one to 12 carbon atoms and is selected from the group consisting of alkyl, alkoxyalkyl, cycloalkyl and aralkyl.

2. A phenanthrene diester in accordance with claim 1 in which R is alkyl having from one to four carbon atoms.

3. A phenanthrene diester in accordance with claim 2 in which R is methyl.

4. A phenanthrene diester in accordance with claim 2 in which R is ethyl.

5. A phenanthrene diester in accordance with claim 2 in which R is propyl.

6. A phenanthrene diester in accordance with claim 2 in which R is butyl.

7. A phenanthrenedicarboxylic acid selected from the group consisting of 1,8-, 2,7-, 3,6- and 2,5-phenanthrenedicarboxylic acids.

8. 1,8-phenanthrenedicarboxylic acid in accordance with claim 7.

9. 3,6-phenanthrenedicarboxylic acid in accordance with claim 7.

* * * * *